United States Patent [19]

Wright, Jr. et al.

[11] 4,192,803

[45] Mar. 11, 1980

[54] 5H-PYRROLO[2,1-c][1,4]BENZODIAZEPINE DERIVATIVES

[75] Inventors: William B. Wright, Jr., Woodcliff Lake; Robert A. Hardy, Jr., Ridgewood, both of N.J.

[73] Assignee: American Cyanamid Company, Stamford, Conn.

[21] Appl. No.: 942,588

[22] Filed: Sep. 15, 1978

[51] Int. Cl.$^2$ .................... C07D 487/04; A61K 31/55
[52] U.S. Cl. ................................. 260/243.3; 424/250
[58] Field of Search ...................................... 260/243.3

[56] References Cited

U.S. PATENT DOCUMENTS 3,962,248  6/1976  Schneider ........................ 260/243.3

Primary Examiner—Jose Tovar
Attorney, Agent, or Firm—Edward A. Conroy, Jr.

[57] ABSTRACT

This disclosure describes substituted 11-piperazinyl-5H-pyrrolo[2,1-c][1,4]benzodiazepines useful as antipsychotic or neuroleptic agents.

9 Claims, No Drawings

5H-PYRROLO[2,1-c][1,4]BENZODIAZEPINE DERIVATIVES

BRIEF SUMMARY OF THE INVENTION

This invention relates to new organic compounds and, more particularly, is concerned with novel 11-piperazinyl-5H-pyrrolo[2,1-c][1,4]benzodiazepines which may be represented by the following structural formula:

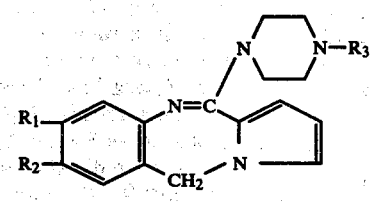

(I)

wherein $R_1$ and $R_2$ are each individually selected from the group consisting of hydrogen, halogen, trifluoromethyl and alkyl whereas $R_3$ is hydrogen, alkyl or β-hydroxyethyl. Suitable alkyl groups contemplated by the present invention are those having up to four carbon atoms such as methyl, ethyl, isopropyl, sec-butyl, etc. whereas halogen is exemplified by fluoro, chloro and bromo.

DETAILED DESCRIPTION OF THE INVENTION

The novel compounds of the present invention are obtainable as crystalline materials having characteristic melting points and absorption spectra. They are appreciably soluble in many organic solvents such as lower alkanols, acetone, ethyl acetate, and the like but are generally insoluble in water. These compounds are organic bases and thus are capable of forming acid-addition salts, formed by admixture of the organic free base with up to two equivalents of an acid, suitably in a neutral solvent. Suitable salts are formed with such acids as sulfuric, phosphoric, hydrochloric, hydrobromic, sulfamic, citric, maleic, fumaric, tartaric, acetic, benzoic, gluconic, ascorbic, and related acids. The acid-addition salts of the novel compounds of the present invention are, in general, crystalline solids relatively soluble in water, methanol and ethanol but relatively insoluble in non-polar organic solvents such as diethyl ether, benzene, toluene, and the like. For purposes of this invention, the free bases are equivalent to their non-toxic acid-addition salts.

The novel compounds of the present invention may be readily prepared as set forth in the following reaction scheme:

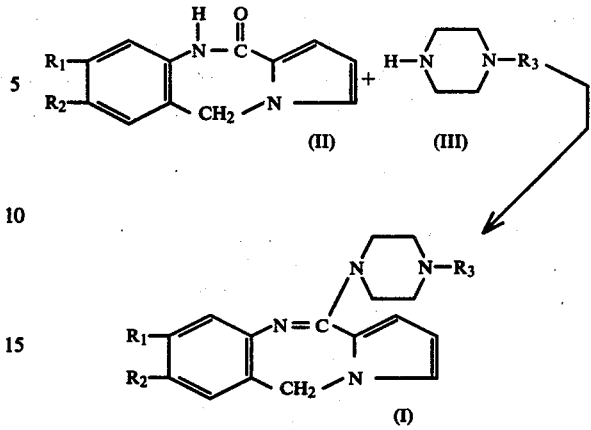

wherein $R_1$, $R_2$ and $R_3$ are as hereinabove defined. In accordance with this reaction scheme, an appropriately substituted 5,10-dihydro-11H-pyrrolo[b 2,1-c][1,4]benzodiazepin-11-one (II) is treated with a mixture of titanium tetrachloride, anisole, and a substituted piperazine (III) in an inert solvent such as benzene, toluene or xylene at 80°-120° C. for a period of 3-24 hours to produce the desired product (I). Alternatively, the starting material (II) may be converted to the corresponding 11-chloro derivative with phosphorus pentachloride in a solvent such as chloroform or carbon tetrachloride at room temperature. The 11-chloro derivative may then be converted to the desired product (I) by treatment with a substituted piperazine (II) in an inert solvent such as benzene, toluene or xylene at 80°-100° C. for a period of 2-5 hours.

Another conversion of lactam (II) to the novel compounds of this invention (I) is illustrated as follows:

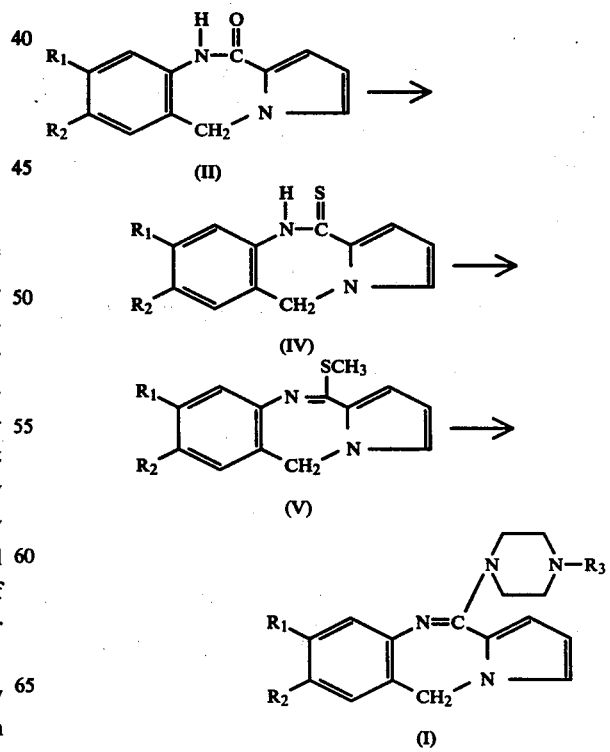

wherein $R_1$, $R_2$ and $R_3$ are as hereinabove defined. By this procedure the lactam (II) is converted to the thiolactam (IV) by treatment with phosphorus pentasulfide, followed by alkylation with methyl iodide to give the 11-methylthio derivative (V). Treatment of (V) with excess piperazine derivative (III), generally in an inert solvent such as toluene or xylene at a temperature from about 80° to 150° C. for a period of 6–24 hours or more, then gives the desired products (I).

Another preparation of the novel compounds of this invention is illustrated by transamination of an 11-amino derivative (VII) as set forth below.

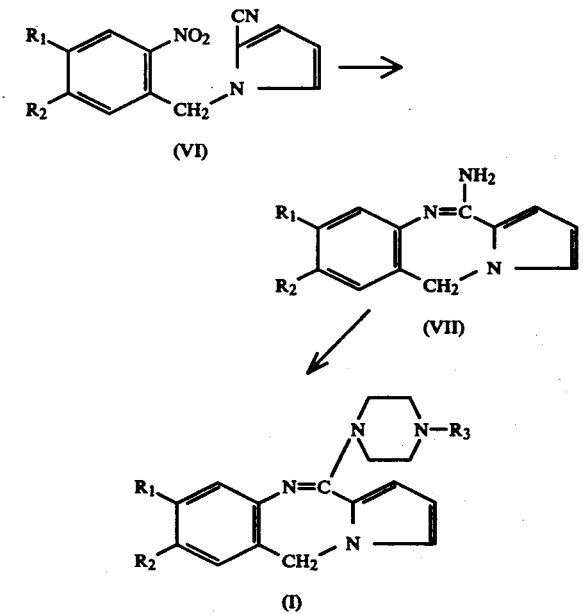

wherein $R_1$, $R_2$ and $R_3$ are as defined hereinabove. By this method an o-nitrobenzylpyrrole-2-carbonitrile (VI), prepared by methods known in the art, is reduced and cyclized (Pinner reaction) to the 11-amino intermediate (VII), followed by treatment with an excess of piperazine derivative (III) at a temperature of from about 80° C. to about 150° C. An acidic catalyst such as ammonium chloride is usually employed.

Another principal method for preparing the novel compounds of the present invention is set forth in the following reaction scheme:

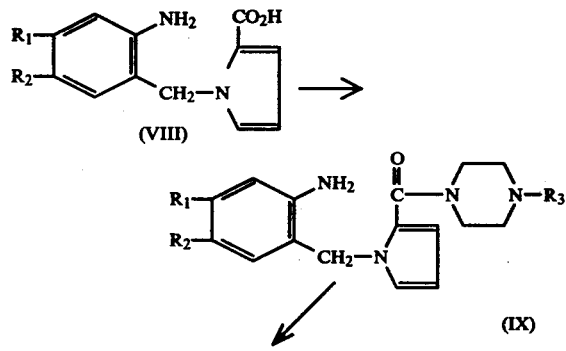

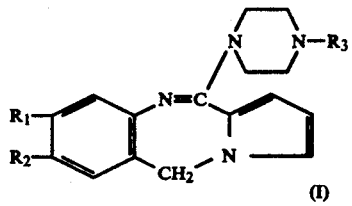

wherein $R_1$, $R_2$ and $R_3$ are as hereinabove defined. In accordance with this reaction scheme, an appropriately substituted 1-(o-aminobenzyl)-2-pyrrolecarboxylic acid (VIII) is treated with a substituted piperazine (III) in an inert solvent such as tetrahydrofuran or dioxane in the presence of carbonyl diimidazole at room temperature for a period of 24–36 hours to provide the corresponding 1-[1-(o-aminobenzyl)-2-pyrrolecarbonyl]piperazine (IX). Cyclization of (IX) is accomplished in phosphorus oxychloride at the reflux temperature for 3–6 hours in the presence of a catalytic amount of dimethylaniline.

Still another principal method for the novel compounds of this invention is set forth in the following reaction scheme:

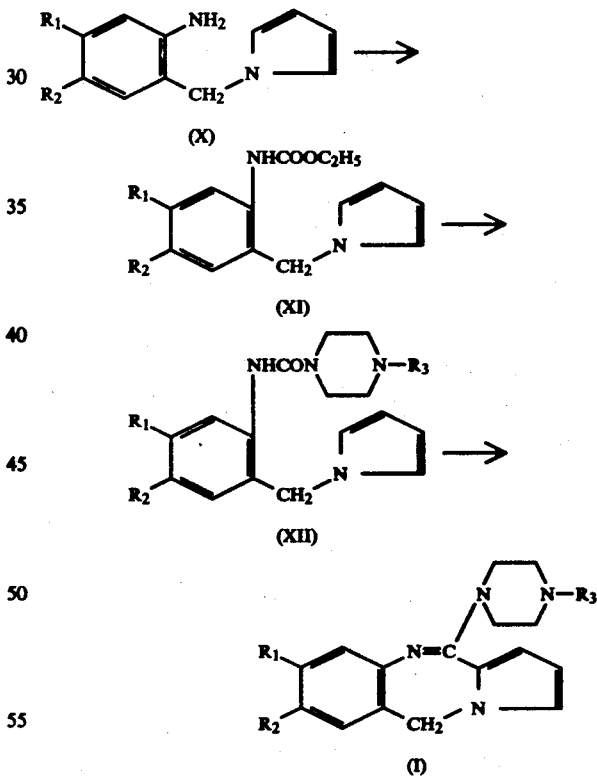

wherein $R_1$, $R_2$ and $R_3$ are as described above. By this route, an o-aminobenzylpyrrole (X) (prepared, for example, by decarboxylation of amino acid (VIII) is converted to the carbanilate derivative (XI) followed by treatment with a suitable piperazine (III) to give the urea derivative (XII). Cyclodehydration of this intermediate (Bishler-Naperialsky reaction) then produces the desired products using methods known to those skilled in the art. Cyclization is effected by dehydrating agents such as phosphorus oxychloride, phosphorus pentoxide, and the like, with or without an inert solvent, and at a temperature from about 80° C. to about 130° C. for about 4–24 hours.

In addition, a combination of procedures may be employed. For example, a product of this invention (I) in which $R_3$ is hydrogen may be prepared by one of the above outlined methods and then converted, by an alkylation procedure, to another new compound of this invention (I) where $R_3$ is alkyl or β-hydroxyethyl.

The compounds of the present invention are physiologically active on the central nervous system and show high activity as anti-psychotic or neuroleptic agents. A useful test for anti-psychotic activity consists of measuring the reduction of spontaneous motor activity in animals. The use of reduced motor activity as a measure of neuroleptic activity has been described by Gray et al., Arch. Int. de Pharmacodyn. et de Therapie 134, 198–215 (1961) and by Kinnard et al. J. Pharmacol. and Exp. Therap. 121, 354–361 (1957). The test compounds are administered orally to groups of four rats at the maximum tolerated dose with the test compound dissolved or suspended in starch vehicle. At an estimated time of peak effect, the rats are placed singly into an Animex ® Activity Counter (Farad Electronics, Sweden) and the activity of each rat is recorded for a five minute period. The activity counts are compared to historical or parallel control values to determine significant decreases in locomotor activity. The compound is considered an active depressant if the activity counts are 50% or less of control values. The results of this test with typical compounds of this invention show neuroleptic activity and are given in Table I below.

Table I

| Compound | Result |
| --- | --- |
| 11-(4-Methyl-1-piperazinyl)-5H-pyrrolo-[2,1-c][1,4]benzodiazepine | Active |
| 7-Chloro-11-(4-methyl-1-piperazinyl)-5H-pyrrolo[2,1-c][1,4]benzodiazepine | Active |
| 8-Chloro-11-(4-methyl-1-piperazinyl)-5H-pyrrolo[2,1-c][1,4]benzodiazepine | Active |

Known antipsychotics such as chlorpromazine and haloperidol protect grouped mice from the lethal effects of d-amphetamine sulfate. Other types of "tranquilizers" such as Librium ® and Valium ® are ineffective. Groups of 10 mice treated orally with the test compounds at a dose of 1 to 20 mg./kg. of body weight. After varying absorption times, the mice are subsequently given intraperitoneal injections of d-amphetamine sulfate at a dose of 15 mg./kg. of body weight. The time of peak effect is established as the absorption time for the respective compounds that protect the greatest percentage of mice from death within 24 hours, with equal to or greater than 50% being considered active. The results of this test with typical compounds of this invention appear in Table II below, establishing the neuroleptic activity of these compounds.

Table II

| Compound | Result |
| --- | --- |
| 11-(4-Methyl-1-piperazinyl)-5H-pyrrolo-[2,1-c][1,4]benzodiazepine | Active |
| 7-Chloro-11-(4-methyl-1-piperazinyl)-5H-pyrrolo[2,1-c][1,4]benzodiazepine | Active |
| 8-Chloro-11-(4-methyl-1-piperazinyl)-5H-pyrrolo[2,1-c][1,4]benzodiazepine | Active |
| 11-(1-Piperazinyl)-5H-pyrrolo[2,1-c]-[1,4]benzodiazepine | Active |

In addition, certain compounds of the present invention show other valuable central nervous system actions, such as antidepressant activity. A useful screening procedure for these actions is inhibition of the depression produced by tetrabenazine hexamate. This general procedure has been described by F. Sulser et al., Ann. N.Y. Acad. Sci. 96, 279 (1962). When tested intraperitoneally in mice, using graded doses of the test compound, 11-(1-piperazinyl)-5H-pyrrolo[2,1-c][1,4]benzodiazepine is active at 12.5 and 25 mg./kg.

The novel compounds of the present invention may be orally administered in compositions such as tablets wherein the principal active ingredient is mixed with conventional tableting ingredients such as corn starch, lactose, sucrose, sorbitol, talc, stearic acid, magnesium stearate, dicalcium phosphate, gums or similar materials as non-toxic pharmaceutically acceptable diluents or carriers. The tablets or pills of the novel compositions can be laminated or otherwise compounded to provide a dosage form affording the advantage of prolonged or delayed action or predetermined successive action of the enclosed medication. For example, the tablet or pill can comprise an inner dosage and an outer dosage component, the latter being in the form of an envelope over the former. The two components can be separated by an enteric layer which serves to resist disintegration in the stomach and permits the inner component to pass intact into the duodenum or to be delayed in release. A variety of materials can be used for such enteric layers or coatings, such materials including a number of polymeric acids or mixtures of polymeric acids with such materials as shellac and cetyl alcohol, cellulose acetate and the like. A particularly advantageous enteric coating comprises a styrene maleic acid copolymer together with known materials contributing to the enteric properties of the coating. The liquid forms in which the novel compounds of the present invention may be incorporated for administration include suitably flavored emulsions with edible oils, such as, cottonseed oil, sesame oil, coconut oil, peanut oil, and the like, as well as elixirs and similar pharmaceutical vehicles.

The term dosage form as described herein refers to physically discrete units suitable as unitary dosage for a warm-blooded animal subject, each unit containing a predetermined quantity of active component calculated to produce the desired therapeutic effect in association with the required pharmaceutical diluent, carrier or vehicle. The dosage may vary from less than one to about 70 mg. per kg. of body weight. Individual unit doses may be from about 10 mg. to about 400 mg. The daily dosage requirement may be from about 50 to 2000 mg. The specification for the novel dosage forms are indicated by characteristics of the active component and the particular therapeutic effect to be achieved or the limitations inherent in the art of compounding such an active component for therapeutic use in warm-blooded animals as disclosed in this specification. Examples of suitable oral dosage forms in accord with this invention are tablets, capsules, pills, powder packets, granules, wafers, cachets, teaspoonfuls , dropperfuls, segregated multiples of any of the foregoing and other forms as herein described.

The invention will be described in greater detail in conjunction with the following specific examples.

EXAMPLE 1

11-(4-Methyl-1-piperazinyl)-5H-pyrrolo[2,1-c][1,4]benzodiazepine

A mixture of 10 g. of 1-(o-aminobenzyl)-2-pyrrolecarbonitrile [M. Artico et al., Il Farmaco Ed. Sci., 24 (11), 980 (1969)], 60 ml. of ethylene glycol and 8 g. of 85% potassium hydroxide is heated in an oil bath at 180° C. for 2 hours, cooled and then diluted with 100 ml. of water. The crystals which form are collected by filtration and recrystallized from 95% ethanol, giving pure 5,10-dihydro-11H-pyrrolo[2,1-c][1,4]-benzodiazepin-11-one. The aqueous mother liquor, when treated with acetic acid to pH 4-5, gives 1-o-aminobenzyl-2-pyrrolecarboxylic acid.

A solution of 23 ml. of N-methylpiperazine in 15 ml. of toluene is added under nitrogen, with cooling and stirring to a mixture of 150 ml. of dry toluene, 12.5 ml. of anisole and 6.3 ml. of titanium tetrachloride. An 11 g. portion of 5,10-dihydro-11H-pyrrolo[2,1-c][1,4]benzodiazepin-11-one and 11.5 g. of N-methylpiperazine are added and the mixture is heated at reflux (about 112° C.) for 5 hours. The reaction mixture is cooled and 20 ml. of isopropanol, 12 g. of celite and 18 ml. of ammonium hydroxide are added. The mixture is stirred and cooled to about 30° C. and 150 ml. of toluene is added. The precipitate is removed by filtration and washed with toluene. The toluene layer is washed with water and then concentrated to remove the solvent. The residue is treated with 70 ml. of 1 N acetic acid and the insoluble material is removed by filtration and discarded. The acetic acid filtrate is extracted once with benzene. The benzene extract is discarded.

The acetic acid filtrate is then treated with an excess of 1 N ammonium hydroxide. The product is extracted into benzene. The benzene layer is washed with water and then concentrated to a residue. The residue is recrystallized from ethanol giving the desired product, m.p. 139°-141° C. The fumarate salt, which is derived by conventional means melts at 208°-210° C.

EXAMPLE 2

7,8-Dichloro-11-(4-methyl-1-piperazinyl)-5H-pyrrolo[2,1-c][1,4]benzodiazepine

Following the general procedure of Example 1, 1-(2-amino-4,5-dichlorobenzyl)-2-pyrrolecarbonitrile is converted to 7,8-dichloro-5,10-dihydro-11H-pyrrolo[2,1-c][1,4]benzodiazepin-11-one and thence to the title compound.

EXAMPLE 3

11-(4-Methyl-1-piperazinyl)-5H-pyrrolo[2,1-c][1,4]benzodiazepine

A mixture of 3.40 g. of carbonyl diimidazole and 25 ml. of tetrahydrofuran is cooled and 4.32 g. of 1-o-aminobenzyl-2-pyrrolecarboxylic acid is added. The mixture is allowed to stand at 25°-30° C. for 30 minutes and 2.6 ml. of N-methylpiperazine is added. The mixture is allowed to stand 48 hours, then concentrated to about ½ volume and treated with ether. The mixture is filtered. The filtrate is evaporated to remove the solvent. The residue is treated with water and methylene chloride. The methylene chloride layer is separated and concentrated and further purified by partition chromatography giving 1-[1-(o-aminobenzyl)-2-pyrrolecarbonyl]-4-methylpiperazine as a viscous oil.

A mixture of 2.8 g. of the above oil, 15 ml. of phosphorous oxychloride and 0.6 ml. of dimethylaniline is heated at 100° C. for 6 hours and then concentrated to remove the volatile material. The gummy residue is treated with water and made strongly basic with ammonium hydroxide. The reaction mixture is extracted with benzene and the benzene layer is washed with water and concentrated. The residue is dissolved in aqueous acetic acid, extracted with benzene (discard extract) and made alkaline with dilute ammonium hydroxide. The mixture is extracted into benzene and the extract is concentrated to remove the solvent. The residue is recrystallized from ethanol giving the desired product as the base, m.p. 139°-141° C.

EXAMPLE 4

8-Methyl-11-(4-ethyl-1-piperazinyl)-5H-pyrrolo[2,1-c][1,4]benzoidazepine

Treatment of 1-(2-amino-4-methylbenzyl)-2-pyrrolecarboxylic acid with N-ethylpiperazine by the procedure described in Example 3 followed by cyclization is productive of the title compound.

EXAMPLE 5

7-Chloro-11-(4-methyl-1-piperazinyl)-5H-pyrrolo[2,1-c][1,4]benzodiazepine

A mixture of 8 g. of 1-(2-amino-5-chlorobenzyl)-2-pyrrolecarbonitrile, 8 g. of 86% potassium hydroxide and 50 ml. of ethyleneglycol is heated in an oil bath at 170° C. for 2 hours. The mixture is partly cooled and diluted with 80 ml. of water. The mixture is cooled for about 3 hours and then filtered. The filtrate is treated with acetic acid to pH 4-5 giving a precipitate which is collected and washed with water. This solid is further purified by dissolving in dilute alkali and reprecipitating with acetic acid, giving 1-(2-amino-5-chlorobenzyl)-2-pyrrolecarboxylic acid.

A mixture of 3.2 g. of the above product, 2.14 g. of carbonyldiimidazole and 35 ml. of tetrahydrofuran is stirred for one hour with cooling in an ice bath, allowed to stand overnight at room temperature, heated at reflux for one hour, diluted with water and concentrated to remove the tetrahydrofuran. The gummy product is extracted into methylene chloride, washed with dilute sodium hydroxide and then water, concentrated and purified by partition chromatography, giving 7-chloro-5,10-dihydro-11H -pyrrolo[2,1-c][1,4]benzodiazepin-11-one.

A mixture of 15 ml. of dry toluene, 1.5 ml. of anisole and 0.8 ml. of titanium tetrachloride is cooled under argon. A solution of 2.8 ml. of N-methylpiperazine in 10 ml. of toluene is added. A 1.55 g. portion of 7-chloro-5,10-dihydro-11H-pyrrolo[2,1-c][1,4]benzodiazepin-11-one and 1.4 ml. of N-methylpiperazine are added in succession. The reaction mixture is heated at reflux for 5 hours, cooled to 60° C. and 2.2 ml. of isopropanol, 2 ml. of concentrated ammonium hydroxide and 1 g. of celite are added. After cooling to 30° C., 20 ml. of toluene are added and the mixture is filtered and washed with toluene. The toluene layer is washed twice with water, concentrated to remove the solvent and cooled. The solid is washed onto a filter with hexane, treated with 10 ml. of 1 N acetic acid and the insoluble material is collected and washed with water. The aqueous layer is treated with 10 ml. of 1 N ammonium hydroxide. The precipitate is collected, washed with water, dried in vacuo and recrystallized from ethanol, giving the desired product, m.p. 186°–188° C.

EXAMPLE 6

7-Ethyl-11-[4-(β-hydroxyethyl)-1-piperazinyl]-5H-pyrrolo[2,1-c][1,4]benzodiazepine In the manner described in Example 5, reaction of 1-(2-amino-5-ethylbenzyl)-2-pyrrolecarboxylic acid with N-(β-hydroxyethyl)piperazine provides the title compound after cyclization.

EXAMPLE 7

8-Chloro-11-(4-methyl-1-piperazinyl)-5H-pyrrolo[2,1-c][1,4]benzodiazepine

A mixture of 5.7 g. of 1-(2-amino-4-chlorobenzyl)-2-pyrrolecarboxylic acid (prepared by the method of Example 5, using 1-(2-amino-4-chlorobenzyl)-2-pyrrolecarbonitrile), 3.9 g. of N,N'-carbonyldiimidazole and 60 ml. of tetrahydrofuran is stirred with cooling for one hour, allowed to stand at room temperature, heated on a steam bath for one hour, diluted with 5 ml. of water and concentrated to remove the tetrahydrofuran. The residue is dissolved in methylene chloride, washed successively with water, 25 ml. of 1 N sodium hydroxide and water, dried over magnesium sulfate and concentrated to remove the solvent. The resulting viscous oil is dissolved in 20 ml. of ethyl acetate and cooled giving crystals. These crystals are heated at 105° C. for one hour and then triturated with ethyl acetate giving 8-chloro-5,10-dihydro-11H-pyrrolo[2,1-c][1,4]-benzodiazepin-11-one.

The above product is converted to 8-chloro-11-(4-methyl-1-piperazinyl)-5H-pyrrolo[2,1-c][1,4]benzodiazepine by the method described in Example 5, m.p. 177°–179° C.

EXAMPLE 8

7,8-Dibromo-11-(4-methyl-1-piperazinyl)-5H-pyrrolo[2,1-c][1,4]benzodiazepine

The general procedure of Example 7 is repeated but replacing the 1-(2-amino-4-chlorobenzyl)-2-pyrrolecarbonitrile employed in that example with an equivalent amount of 1-(2-amino-4,5-dibromobenzyl)-2-pyrrolecarbonitrile whereby there is obtained the title compound.

EXAMPLE 9

11-(4-Methyl-1-piperazinyl)-5H-pyrrolo-[2,1-c][1,4]benzodiazepine

A mixture of 2 g. of 5,10-dihydro-11H-pyrrolo[2,1-c][1,4]benzodiazepin-11-one (Example 1), 2 g. of phosphorus pentachloride and two drops of N,N-dimethylformamide in 50 ml. of toluene is heated on the steam bath for several hours. The solvent is removed by distillation, 25 ml. of chloroform is added and the mixture evaporated again. The residue is dissolved in 25 ml. of chloroform and this solution slowly added to 10 ml. of N-methylpiperazine in 40 ml. of toluene. This mixture is heated for several hours, finally to the boiling point of toluene, and then evaporated to an oily residue. The residue is taken up in ether (500 ml) and extracted into dilute acetic acid. The aqueous acetic acid layer is made basic with concentrated ammonium hydroxide and the product which precipitates is extracted into ether. The ether solution is dried over anhydrous potassium carbonate, and evaporated to a residue which contains the desired product. When purified by recrystallization it shows m.p. 139°–141° C. (base).

EXAMPLE 10

11-(1-Piperazinyl)-5H-pyrrolo[2,1-c][1,4]-benzodiazepine

A mixture of 6.0 g. of 5,10-dihydro-11H-pyrrolo[2,1-c]-[1,4]benzodiazepin-11-one (Example 1), 2.64 g. of phosphorus pentasulfide and 50 ml. of pyridine is stirred and heated at the reflux temperature for 4 hours, and concentrated to remove the pyridine. The residue is treated with 75 ml. of 5% aqueous sodium bicarbonate solution and 5 ml. of methanol and stirred at room temperature overnight. The product crystallizes gradually and is collected, washed with water and dried. This crude product is dissolved in chloroform, passed through a bed of Magnesol ® silica gel, and the solvent evaporated to give yellow crystals of 5,10-dihydro-11H-pyrrolo[2,1-c][1,4]benzodiazepin-11-thione, m.p. 228°–231°.

The above thione (3.85 g) is added to a solution of 0.42 g. of sodium in 60 ml. of ethanol, and the mixture is stirred for 1 hour. Methyliodide (1.8 ml) is added and stirring continued for about 4 hr. The product separates as a yellow precipitate, is collected and washed with ethanol and dried; 11-methylthio-5H-pyrrolo[2,1-c][1,4]benzodiazepine, m.p. 152°–154° C. is thereby obtained.

A mixture of 1.55 g. of 11-methylthio derivative, 7 ml. of piperazine, 4 drops of acetic acid and 15 ml. of xylene is heated to the refluxing temperature for 48 hr. and concentrated under reduced pressure to remove xylene and most of the piperazine. The residue is diluted with water and filtered; the solid crystals are stirred with 50 ml. of 2 N acetic acid, the insoluble portion (starting material) filtered off, and the filtrate neutralized with 7 ml. of concentrated ammonium hydroxide. The desired product is thereby precipitated and it is extracted into dichloromethane, the organic phase washed with water, dried over magnesium sulfate, and concentrated to remove the solvent. Trituration of the residue with ether then gives 11-(1-piperazinyl)-5H-pyrrolo[2,1-c][1,4]benzodiazepine, m.p. 148°–150° C., when collected and dried in a vacuum oven.

EXAMPLE 11

11-(1-Piperazinyl)-5H-pyrrolo[2,1-c][1,4]-benzodiazepine

A mixture of 20 g. of 1-(o-nitrobenzyl)-2-pyrrolecarbonitrile [M. Artico et al.; See Example 1], 50 g. of zinc dust, 40 ml. of glacial acetic acid and 200 ml. of ethanol is stirred at room temperature for about 24 hr. The reaction mixture is filtered to remove unreacted zinc dust and the precipitate is washed with alcohol. The filtrate is chilled to 0° C. and the precipitated zinc salts are removed by filtration; this filtrate is then evaporated to a solid residue which is dissolved in methylene chloride and filtered again. The solvent is removed by evaporation and the residue crystallized by the addition of ether; the product is collected and 11-amino-5H-pyrrolo[2,1-c]-[1,4]benzodiazepine, m.p. 179°–181° C., is thereby obtained.

The above 11-amino compound (4.5 g), 20 g. of anhydrous piperazine, 2 g. of ammonium chloride and 20 ml. of toluene are heated at the reflux temperature for about 6 hr. The reaction mixture is then diluted with water and evaporated to a semi-solid residue. This residue is taken up in water and a gummy solid remains insoluble; the aqueous layer is decanted, the residue is dissolved in ether, and the solvent evaporated. The crude product is dissolved in dilute hydrochloric acid, the mixture filtered, and the filtrate made basic with concentrated ammonium hydroxide. The solid precipitate is extracted into methylenechloride, the organic layer dried over anhydrous potassium carbonate, and then evaporated to a solid. The desired product is then obtained by fractional crystallization from ether, extracting the crude solid with successive portions of boiling diethyl ether (approx. 100 ml) filtering the insoluble material, concentrating the ether filtrate to small volume and crystallization in the cold; 11-(1-piperazinyl)-5H-pyrrolo[2,1-c]-[1,4]benzodiazepine, identical with the same compound prepared as described in Example 10, is thereby obtained.

EXAMPLE 12

11-(4-Methyl-1-piperazinyl)-5H-pyrrolo[2,1-c][1,4]-benzodiazepine 1-(o-Aminobenzyl)-2-pyrrolecarboxylic acid, prepared by hydrolysis of 1-(o-aminobenzyl)-2-pyrrolecarbonitrile (Example 1) with potassium hydroxide (Example 1), is heated above its melting point for several minutes (245°–250° C.). After the evolution of gases ceases the residue is cooled, taken up in methylene chloride, and a small amount of precipitate is filtered. The filtrate is evaporated and the residue is crystallized with the aid of petroleum ether to give 1-(o-aminobenzyl)pyrrole.

The above aminobenzyl-pyrrole is converted to ethyl o-(1-pyrrolylmethyl)carbanilate by treatment with ethyl chloroformate, and this carbanilate upon heating with an excess of N-methylpiperazine is then transformed to 4-methyl-2′-(1-pyrrolylmethyl)-1-piperazinecarboxanilide. The piperazinecarboxanilide is cyclized (Bischler-Napieralsky cyclodehydration) by heating with a mixture of phosphorus oxychloride and phosphorus pentoxide. 11-(4-Methyl-1-piperazinyl)-5H-pyrrolo[2,1-c][1,4]benzodiazepine, identical with the properties described in Example 1, is thereby obtained.

EXAMPLE 13

11-(1-Piperazinyl)-8-trifluoromethyl-5H-pyrrolo[2,1-c][1,4]benzodiazepine 1-(2-Amino-5-trifluoromethylbenzyl)-2-pyrrolecarbonitrile is converted to 7-trifluoromethyl-5,10-dihydro-11H-pyrrolo-[2,1-c][1,4]benzodiazepin-11-one by the general methods described in Example 5.

This trifluoromethyl-benzodiazepinone, following the procedures of Example 10, is treated with phosphorus pentasulfide to give the 11-thione, followed by sodium ethylate and methyl iodide to give the 11-methylthio derivative which is heated with an excess of anhydrous piperazine; 11-(1-piperazinyl)-8-trifluoromethyl-5H-pyrrolo[2,1-c][1,4]benzodiazepine is thereby obtained.

EXAMPLE 14

8-Fluoro-11-(1-piperazinyl)-5H-pyrrolo-[2,1-c][1,4]benzodiazepine 1-(5-Fluoro-2-nitrobenzyl)-2-pyrrolecarbonitrile is treated with zinc dust, acetic acid and ethanol, by the general procedures described in Example 11, and 11-amino-8-fluoro-5H-pyrrolo[2,1-c][1,4]benzodiazepine is obtained. Heating this intermediate with an excess of anhydrous piperazine then produces the subject compound.

EXAMPLE 15

11-[4-(2-Hydroxyethyl)-1-piperazinyl]-5H-pyrrolo[2,1-c][1,4]benzodiazepine 11-(1-Piperazinyl)-5H-pyrrolo[2,1-c][1,4]benzodiazepine is treated with ethylene oxide and the above compound is thereby obtained.

We claim:

1. A compound selected from the group consisting of those of the formula:

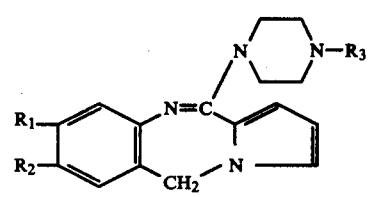

wherein $R_1$ and $R_2$ are each individually selected from the group consisting of hydrogen, halogen, $CF_3$ and alkyl having from 1 to 4 carbon atoms and $R_3$ is selected from the group consisting of hydrogen, alkyl having from 1 to 4 carbon atoms and β-hydroxyethyl; and the pharmacologically acceptable acid-addition salts thereof.

2. The compound according to claim 1 wherein $R_1$ and $R_2$ are both methyl and $R_3$ is ethyl; 7,8-dimethyl-11-(4-ethyl-1-piperazinyl)-5H-pyrrolo[2,1-c][1,4]benzodiazepine.

3. The compound according to claim 1 wherein $R_1$ and $R_2$ are both hydrogen and $R_3$ is methyl; 11-(4-methyl-1-piperazinyl)-5H-pyrrolo[2,1-c][1,4]benzodiazepine.

4. The compound according to claim 1 wherein $R_1$, $R_2$ and $R_3$ are each hydrogen; 11-(1-piperazinyl)-5H-pyrrolo[2,1-c]-[1,4]benzodiazepine.

5. The compound according to claim 1 wherein $R_1$ is chloro, $R_2$ is hydrogen and $R_3$ is methyl; 8-chloro-11-(4-methyl-1-piperazinyl)-5H-pyrrolo[2,1-c][1,4]benzodiazepine.

6. The compound according to claim 1 wherein $R_1$ is hydrogen, $R_2$ is chloro and $R_3$ is methyl; 7-chloro-11-(4-methyl-1-piperazinyl)-5H-pyrrolo[2,1-c][1,4]benzodiazepine.

7. The compound according to claim 1 wherein $R_1$ is fluoro, and $R_2$ and $R_3$ are both hydrogen; 8-fluoro-11-(1-piperazinyl)-5H-pyrrolo[2,1-c][1,4]benzodiazepine.

8. The compound according to claim 1 wherein $R_1$ is trifluoromethyl, and $R_2$ and $R_3$ are both hydrogen; 11-(1-piperazinyl)-8-trifluoromethyl-5H-pyrrolo[2,1-c][1,4]benzodiazepine.

9. The compound according to claim 1 wherein $R_1$ and $R_2$ are both hydrogen and $R_3$ is hydroxyethyl; 11-[4-(2-hydroxyethyl)-1-piperazinyl]-5H-pyrrolo[2,1-c][1,4]benzodiazepine.

* * * * *